United States Patent [19]
Allonen et al.

[11] Patent Number: 5,558,637
[45] Date of Patent: Sep. 24, 1996

[54] IMPLANT INJECTION DEVICE

[75] Inventors: Hannu Allonen, Kirjala; Pekka Lankinen, Turku; Matti Lehtinen, Piispanristi, all of Finland

[73] Assignee: Leiras Oy, Turku, Finland

[21] Appl. No.: 309,019

[22] Filed: Sep. 20, 1994

[30] Foreign Application Priority Data

Oct. 13, 1993 [FI] Finland .................................. 934513

[51] Int. Cl.$^6$ .................................................. A61M 31/00
[52] U.S. Cl. .............................. 604/60; 604/110; 604/263
[58] Field of Search .................... 604/57, 59, 60, 604/68, 110, 192, 197, 198, 199, 256, 263, 181, 187, 218, 220; 120/919

[56] References Cited

U.S. PATENT DOCUMENTS

| | | | |
|---|---|---|---|
| 2,857,912 | 10/1958 | Feinstone et al. | 604/199 X |
| 3,780,735 | 12/1973 | Crouter et al. | 128/223 |
| 4,601,699 | 7/1986 | Crain | 604/64 |
| 4,826,483 | 5/1989 | Molnar, IV | 604/110 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,215,536 | 6/1993 | Lampropoulos et al. | 604/187 X |
| 5,370,620 | 12/1994 | Shonfeld | 604/110 |
| 5,380,295 | 1/1995 | Vacca | 604/187 |
| 5,423,756 | 6/1995 | van der Merwe | 604/218 X |

*Primary Examiner*—Corrine M. McDermott
*Assistant Examiner*—N. Kent Gring
*Attorney, Agent, or Firm*—Ronald J. Kubovcik, Esq.

[57] ABSTRACT

An implant injection device for once-only use includes an elongated implant housing (10), a cannula (11) and a plunger (20) which is longitudinally movable in the implant housing. The surface (21) of the plunger and the inner wall (15) of the implant housing are equipped with interacting projections (22, 12) which permit the plunger to move inwards into the implant housing but which prevent the removal of the plunger from the implant housing.

16 Claims, 2 Drawing Sheets

IMPLANT INJECTION DEVICE

FIELD OF INVENTION

This invention relates to an injection device for once-only use for injecting implants.

BACKGROUND OF THE INVENTION

Devices for the injection of implants have been described earlier in the patent literature. As examples of patent publications disclosing various injection devices for implants can be mentioned EP 304700, EP 304107, WO 8806905, U.S. Pat. No. 4,451,254 and GB 2199247. EP 304700 discloses a device the sterility of which has been improved by preventing the plunger from accidentally coming out from the housing. The housing is made of plastic but the cannula and the plunger are made of metal. EP 304107 discloses a device intended for once-only use for injecting implants in which device the housing is made of plastic but the cannula is made of metal. The patent concerns particularly an element connected with the plunger, the function of which element is to prevent the implant from being pushed forwards too early, i.e. during the puncture of the skin. WO 8806905 relates to a complicated device intended for repeated use for subcutaneous implantation in a desired manner of a plurality of sucessive implants situated in said device. The invention concerns particularly equipment for the application of the implants. U.S. Pat. No. 4,451,254 discloses also an implanter for the application of several implants said implanter being intended for repeated use, wherein the implants are fed from a cartridge mounted to the side of the implanter. The publication GB 2199247 describes equipment for the implantation of hormone implants wherein said device, which is intended for once-only use, is completely made of plastic. First an incision is made into the skin with a scalpel after which a trocar attached to the cannula is pushed to a desired depth beneath the skin. The trocar, the opposite end of which is blunt, is withdrawn and again inserted in the cannula with the blunt end forwards touching the implant, wherein the blunt end is used as plunger. The implant injection devices described above exhibit several disadvantages and faults.

A great risk related to devices intended for once-only use is therein that these devices may come into the hands of misusers of drugs and related substances. The device intended for once-only use as described in the European patent publication EP 304107 would be very easy to use after the removal of its contents of original implants. The plunger can freely be withdrawn from the medical container after which the container easily can be loaded with new substances. The injection device for implants as described in the patent publication EP 304700 contains a flexible ring fitted onto the inner surface of the medical container, said ring interacting with an annular groove in the plunger. The ring and annular groove retard the back and forth motion of the plunger in the medical container so that the plunger will not accidentally come out from the medical container. They also prevent the plunger from accidentally moving forwards before the implants are going to be administered. However, if greater pushing or pulling forces are applied to the plunger, the plunger is enabled to move both inwards and outwards and there is nothing preventing the plunger from being completely drawn out. The reuse of the device intended for once-only use as described in GB 2199247 is not prevented by any means.

The sterilization of the devices for once-only use is preferably performed by gas, e.g. ethylene oxide gas, at the stage when all the components including the implants are fitted in the implant container. Sterilization by gamma radiation represents in principle another alternative for sterilization. It suffers, however, from the disadvantage due to the fact that it is not tolerated by all pharmaceutical substances. As a result thereof, the possibilities of application of gas sterilization are much wider. The once-only usage device according to the EP 304107 patent cannot be sterilized by gas after putting the parts together because there are no passages through which the gas would be permitted to penetrete into the inner part of the device.

The manufacturing costs of devices for once-only use must of course be low. It would be desirable to have all components of the device manufactured of plastic. The cannula creates a problem because it must be equipped with a sharp edge to enable the incision of the skin. In all the constructions described in prior art except for the decive disclosed in GB 2199247 the cannula has been made of metal. The device for once-only use according to EP 304107 is otherwise made of plastic but in the manufacturing of the cannula it has been necessary to use metal as manufacturing material.

SUMMARY OF THE INVENTION

The objective of this invention is to overcome the problems described above and to provide a novel once-only use injection device for implants which does not suffer from the drawbacks disclosed above.

Thus, the object of the present invention is an implant injection device for once-only use said device comprising an elongated implant housing, a cannula and a plunger which is longitudinally movable in the implant housing. The device is characterized in that the surface of the plunger and the inner wall of the implant housing are equipped with interacting projections which permit the plunger to move inwards into the implant housing but which prevent the removal of the plunger from the implant housing.

The invention provides a safe once-only use injection device for implants which after use in the hands of unauthorized persons not any longer would be useful for administration of any substances because the plunger cannot be removed from the implant housing without destroying it. According to another preferred embodiment of the invention the implant housing, the cannula and the plunger are made of plastic. To protect the cannula before use it is preferably equipped with a protecting cap which also can be made of plastic.

According to a third preferred embodiment the surfaces of the implant housing and the cannula as well as the protecting cap are perforated with holes through which the sterilization gases are allowed to penetrate. This construction enables gas sterilization of the complete device into which implants have been inserted.

According to a fourth preferred embodiment an incision edge is attached to the body, e.g. to the protecting cap of the device. The incision edge is used to make an incision in the skin before the plastic cannula is pushed beneath the skin. In order to protect the incision edge before use and afterwards, a projective part has been made in close proximity to the incision edge.

BRIEF EXPLANATION OF THE DRAWINGS

The invention will be explained in more detail by reference to the attached drawings wherein.

PREFERRED EMBODIMENT OF THE INVENTION

Figure 1:
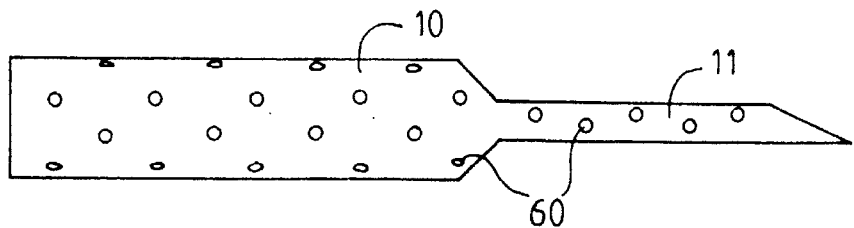
FIG. 1 illustrates a side view of the of the implant housing and the cannula attached hereto
Figure 4:
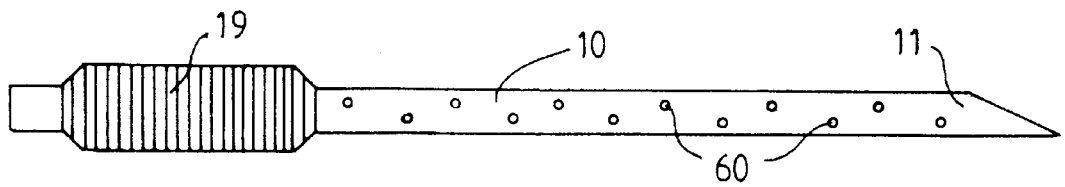
FIG. 4 shows a side view of the implant housing and the cannula in one piece according to another embodiment
Figure 5:
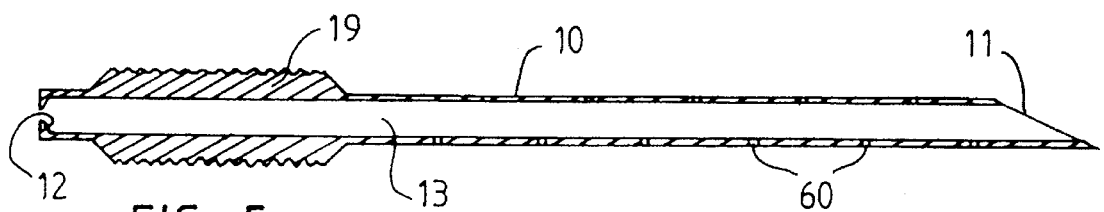
FIG. 5 shows a longitudinal section of the device of FIG. 4

FIG. 1 shows a side view of the implant housing 10 and the cannula 11 attached hereto. The implant housing as well as the cannula are perforated with holes 60 to enable gas sterilization of the device. The implant housing and the cannula can be different pieces attached to each other afterwards. Alternatively these components can be made in one piece. FIGS. 4 and 5 show a construction where the implant housing and the cannula are in one piece so that one end of the housing forms the cannula. The handle is marked with reference number 19.

Figure 2:
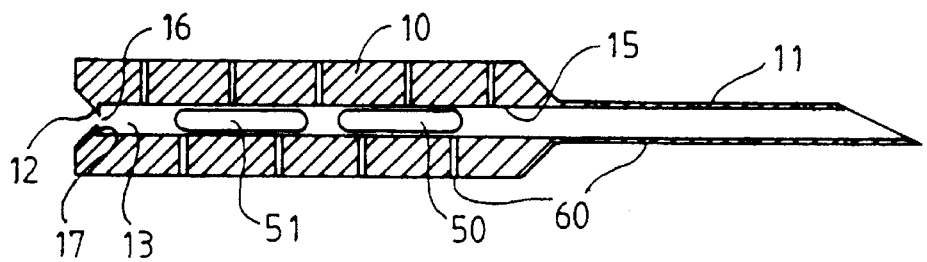
FIG. 2 shows a longitudinal section of the device of FIG. 1 loaded with implants
Figure 3:
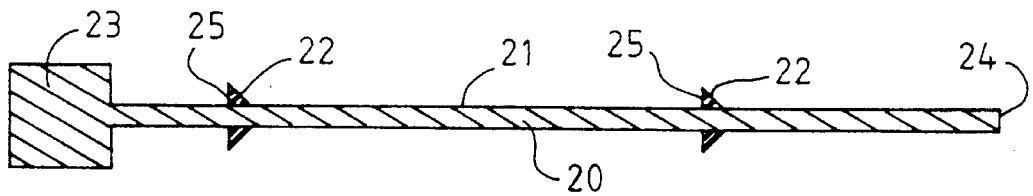
FIG. 3 shows a longitudinal section of the plunger of the device

FIG. 2 shows a longitudinal section of the implant housing and a cannula attached hereto wherein the implant housing is loaded with two implants 50 and 51. The first end 24 of the plunger 20 of FIG. 3 is pushed in the channel 13 of the implant housing and the opposite end of the plunger ends in the pushbutton 23. The surface 21 of the plunger has been equipped with projections 22 which surround the surface of the plunger. The projections 22 may be attached to the plunger in a separate stage afterwards or, alternatively, the plunger and the projections 22 may be manufactured in one piece. The purpose of the projections 22 is to prevent the plunger from being removed from the implant housing. Onto the end of the implant housing directed away from the cannula has been shaped an edge 12 at the position 16 of which the area of the channel 13 in the implant housing is restricted. The projections 22 have been shaped so as to bend in direction towards the pushbutton when the plunger is pushed inwards in the the implant housing and are therefore able to penetrate the restricted area 16. On the other hand, when one tries to withdraw the plunger out of the implant housing the surface 25 of the projection 22 touches the surface 17 of the edge, which extends perpendicularly from inner wall 15, in the restricted area. The movement of the plunger stops because the projections 22 cannot bend enough in direction towards the cannula so as to allow their penetration of the restricted area 16. There may be only one single projection 22 but preferably the projections are two as shown in FIG. 3, or even more. When the projection 22 in proximity to the cannula has been pushed into the implant housing it safeguards that the plunger will not come out during the use of the device. After the last projection, i.e. the projection 22 in proximity to the pushbutton 23 has been pushed into the implant housing it safeguards that the device cannot be reused for the injection of other substances because the plunger cannot be removed from the implant housing. Preferably the section of the projection 22 is approximately shaped as a half of a dovetail which broadens towards the pushbutton 23 of the plunger.

Figure 9:
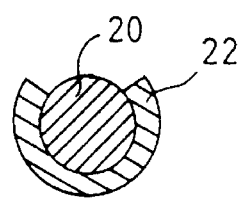
FIG. 9 shows a cross section of the projection surrounding the plunger according to one embodiment
Figure 10:
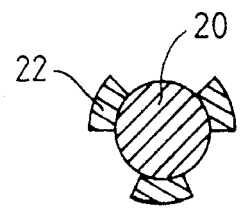
FIG. 10 shows a cross section of the projection surrounding the plunger according to another embodiment

The projection 22 can be a continuous annular piece surrounding the surface 21 of the plunger. Alternatively it can consist of one or several parts attached to the surface 21 of the plunger to form a surrounding open or discontinuous ring as shown in FIGS. 9 and 10.

The material of the projection 22 must be flexible enough so as to allow the plunger to be pushed into the implant housing. On the other hand the material must be stiff enough to prevent the plunger from being removed therefrom.

Figure 6:
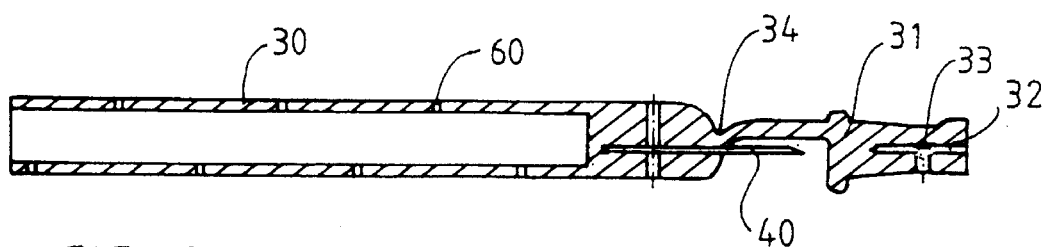
FIG. 6 shows a longitudinal section of the protecting cap for the cannula the end of said protecting cap being equipped with an incision edge and a projective part for the protection of the incision edge

FIG. 6 shows the protecting cap 30 for the cannula which cap also is perforated with holes 60 in order to enable gas sterilization. Because the cannula 11 is made of plastic it is not as such sharp enough to make an incision in the skin and therefore a separate device is needed. For this purpose a separate incision edge 40 has been attached to the end of the cap 30. For the protection of the incision edge a projective part 31 has been arranged in the close proximity of the incision edge. The projective part partially surrounds the head of the edge 40. The projective part forms preferably one single piece together with the protecting cap 30. When the device is taken into use the projective part 31 is bent upwards, i.e. in the direction away from the edge 40, after which it breaks along the break-line made at position 34. When an incision has been made into the skin with the edge 40, the edge 40 can be pushed into the groove 32 of the released protecting part 31. The groove 32 is equipped with a fixing means 33 (for example a knob) which is fixable to a corresponding means 41 (for example a hole) arranged into the edge 40. In this way it can be safeguarded that the edge 40 after the use is protected and does not cause dangerous situations in the destroying stage.

Figure 7:
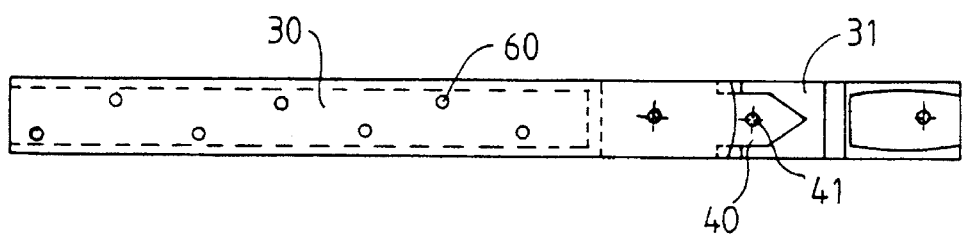
FIG. 7 shows a side view of the device of FIG. 6 seen from the edge side
Figure 8:
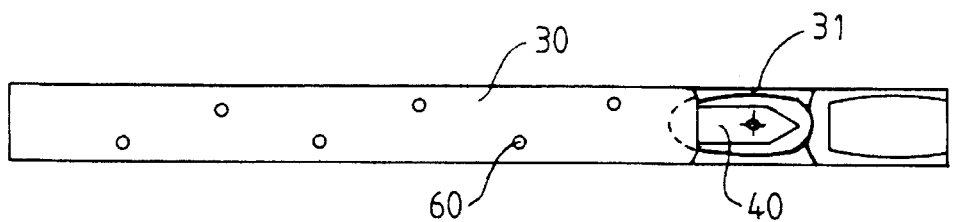
FIG. 8 shows the device of FIG. 7 according to another embodiment

In the construction shown by FIGS. 6 and 7 the projective part 31 protecting the incision edge forms a uniform piece on one side of the edge (in FIG. 6 above the edge). FIG. 8 illustrates another construction wherein the projective part 31 forms an halfcircle-shaped projections surrounding the periphery of the incision edge 40.

The incision edge 40 and the protecting projective part 31 may be attached to another part of the body of the device, e.g. to the implant housing or to the pushbutton of the plunger because due to the protecting projective part the edge is well protected in its groove after use. The most suitable place for the edge to be attached to is the protecting cap of the cannula because this component has no use during the injection.

According to the construction described above the projection 22 which is flexible to some extent has been attached to the plunger. Alternatively the implant housing can also be equipped with flexible projections while the plunger can be equipped with a rigid projections.

The implant housing and the plunger can also be equipped with means for the calculation of implants administered for example as follows: The plunger can be equipped with two or more pivots on a distance from each other corresponding to the length of one implant. The pivots extend radially in different directions from the surface of the plunger. The edge 12 of the implant housing is equipped with a loop running longitudinally in the direction of the implant housing. Pushing of the plunger into the implant housing becomes possible only by rotating the plunger so that the first pivot runs into the loop. When the plunger has been pushed into the implant housing to a certain distance, for example to a distance corresponding to the length of one implant, the motion of the plunger will be stopped because a second pivot extending in a different direction will stop against the edge 12. Only by rotating the plunger so that the second pivot runs into the loop in the edge 12 the pushing of the plunger into the implant housing can be continued. In this way it can be safeguarded that too many implants will not be administered by mistake.

Suitable plastic materials for the device according to the invention are any non-toxic, constructively stiff enough plastic materials that can be sterilized.

The device according to the invention is intended particularly for the injection of hormone containing implants to be used for prolonged hormonal treatment or as contraceptives. The finished product is preferably supplied as loaded with one or several implants.

Those versed in the art will appreciate that many different variations and adaptions of the present invention fall within the scope of the claims to be presented below.

We claim:

1. A single use implant injection device, said device comprising:

an implant housing having proximal and distal ends and an inner wall defining a channel therethrough, said inner wall having a projection thereon at said proximal end of said housing, said projection extending into said channel;

a cannula extending from said distal end of said housing;

a plunger having proximal and distal ends, said plunger being longitudinally movable in said housing and having a projection thereon at said proximal end, said projection on said plunger and said projection on said inner wall being configured so that said plunger can be inserted in said proximal end of said housing but cannot be removed from said proximal end of said housing; and a cap disposed on said cannula, said cap having an end, said end having an incision edge attached thereto.

2. The implant injection device of claim 1, wherein said projection on said inner wall at said proximal end of said housing has first and second surfaces, said first surface being approximately perpendicular to said inner wall and extending into said channel to engage said projection on said plunger, said second surface having a frustoconical configuration, a diameter of said second surface increasing in the direction of said proximal end of said housing.

3. The implant injection device of claim 2, wherein said plunger has a pushbutton at a proximal end and said projection on said plunger has third and fourth surfaces, said third surface being approximately perpendicular to a surface of said plunger and being closer to said pushbutton than said fourth surface, said fourth surface extending between said third surface and the surface of said plunger.

4. The implant injection device of claim 3, wherein said projection on said plunger is a continuous annular portion surrounding the surface of said plunger.

5. The implant injection device of claim 3, wherein said projection on said plunger comprises at least one portion partially surrounding the surface of said plunger to form an open ring.

6. The implant injection device of claim 2, wherein at least two projections are disposed on the surface of said plunger in a longitudinal direction.

7. The implant injection device of claim 1, wherein a protective portion for covering said incision edge extends from said cap.

8. The implant injection device of claim 7, wherein an end of said protective portion is at least partially bent around a head of said incision edge.

9. The implant injection device of claim 7, wherein said protective portion has a break line for breaking said protective portion away from said cap.

10. The implant injection device of claim 9, wherein said protective portion has a groove formed therein, and said groove and said incision edge are provided with means for fixing said protective portion to said incision edge so that said incision edge can be protected in said groove after use.

11. The implant injection device of claim 7, wherein said incision edge and said protective portion are disposed at an end of said cap.

12. The implant injection device of claim 1, wherein said housing, said cannula, and said plunger are made of plastic.

13. The implant injection device of claim 12, further comprising at least one injectable implant.

14. The implant injection device of claim 13, wherein said implant is a hormone containing implant for prolonged hormonal treatment.

15. The implant injection device of claim 14, wherein said implant is a contraceptive.

16. A single use implant injection device, said device comprising:

an implant housing having proximal and distal ends and an inner wall defining a channel therethrough, said inner wall having a projection thereon at said proximal end of said housing, said projection extending into said channel;

a cannula extending from said distal end of said housing;

a plunger having proximal and distal ends, said plunger being longitudinally movable in said housing and having a projection thereon at said proximal end, said projection on said plunger and said projection on said inner wall being configured so that said plunger can be inserted in said proximal end of said housing but cannot be removed from said proximal end of said housing; and a cap disposed on said cannula, said cap having an end, said end having an incision edge attached thereto, said cap further having a protective portion for covering said incision edge extending therefrom, said protective portion having an end which is at least partially bent around a head of said incision edge and having a groove formed therein, and said groove and said incision edge being provided with means for fixing said protective portion to said incision edge so that said incision edge can be protected in said groove after use.

* * * * *